United States Patent [19]
Eri et al.

[11] Patent Number: 5,116,879
[45] Date of Patent: May 26, 1992

[54] PROCESS USING A SUPPORTED CATALYST FOR HYDROCARBON SYNTHESIS

[75] Inventors: Sigrid Eri, Trondheim, Norway; James G. Goodwin, Jr.; George Marcelin, both of Pittsburgh, Pa.; Trygve Riis, Oslo, Norway

[73] Assignee: Den norske stats oljeselskap a.s., Stavanger, Norway

[21] Appl. No.: 590,430

[22] Filed: Sep. 28, 1990

Related U.S. Application Data

[62] Division of Ser. No. 290,936, Dec. 28, 1988.

[51] Int. Cl.$^5$ .............................................. C07C 1/04
[52] U.S. Cl. ..................................... 518/716; 518/715
[58] Field of Search .............................. 518/715, 718

[56] References Cited

U.S. PATENT DOCUMENTS

| | | |
|---|---|---|
| 3,988,344 | 10/1976 | Nakaoji . |
| 4,088,671 | 9/1978 | Kobylinski . |
| 4,390,734 | 6/1983 | Knifton . |
| 4,396,539 | 8/1983 | Sapienza et al. . |
| 4,568,663 | 2/1986 | Mauldin . |
| 4,595,703 | 6/1986 | Payne et al. . |
| 4,801,573 | 1/1989 | Eri et al. . |
| 4,857,559 | 8/1989 | Eri et al. . |

FOREIGN PATENT DOCUMENTS 221598 10/1986 European Pat. Off. .

OTHER PUBLICATIONS

H. Pichler, *Advances in Catalysis*, vol. IV (1952), pp. 271-272, 299-306.
M. A. Vannice, "The Catalytic Synthesis of Hydrocarbons from $H_2$/CO Mixtures over Group VIII Metals", Journal of Catalysis, 50, pp. 228-236.
*Catalysis*, vol. IV, Reinhold Publishing Co., (1956) pp. 29-33, 46-64.
M. A. Vannice, "Titania Supported Metals as CO Hydrogenation Catalysts" Journal of Catalysis, 74, 199 (1982).

*Primary Examiner*—Howard T. Mars
*Attorney, Agent, or Firm*—Kirkpatrick & Lockhart

[57] ABSTRACT

A process for converting synthesis gas, a mixture of hydrogen and carbon monoxide, into a mixture of predominately paraffinic hydrocarbons using a catalyst which includes catalytically active amounts of cobalt and a loading-insensitive second metal selected from the group consisting of platinum, iridium, rhodium and mixtures thereof, composited on an alumnia support. The finished catalyst exhibits a positive x-ray diffraction pattern. A metal oxide promoter may also be added.

3 Claims, 7 Drawing Sheets

% Conversion vs. Pt Loading
(12% Co/alumina, w. or w/o 1% RE)

% Conversion vs. Ir Loading
(12% Co/alumina, w. 1% RE)

% Conversion vs. Rh Loading
(12% Co/alumina, w. 1% RE)

% Conversion vs. Co Loading
Effect of Pt

□ Without Pt      + With Pt/Co wt. ratio = 0.0085

PROCESS USING A SUPPORTED CATALYST FOR HYDROCARBON SYNTHESIS

This is a divisional application of U.S. application Ser. No. 07/290,936 filed Dec. 28, 1988.

BACKGROUND OF THE INVENTION

1. Field of the Invention

The present invention relates to a catalytic process for converting synthesis gas to hydrocarbons.

2. Description of the Prior Art

The reaction to convert carbon monoxide and hydrogen mixtures (so called syngas) to higher hydrocarbons over metallic catalysts has been known since the turn of the century. This reaction is commonly referred to as the Fischer-Tropsch or F-T synthesis. The F-T synthesis was exploited commercially during WWII in Germany. By 1944 a total of nine F-T plants were operating in Germany, primarily using a catalyst composed of cobalt, magnesium oxide, thorium oxide, and kieselguhr, in the relative composition 100:5:8:200. Later, most of the thoria was replaced by magnesia, primarily for economic reasons. Currently, commercial Fischer-Tropsch plants, which use a precipitated iron-based catalyst which contains various promoters to improve the stability and product distribution, are operating in South Africa.

The common F-T catalysts are nickel, cobalt, and iron. Nickel was probably the first substance to be recognized as capable of catalyzing the reaction of syngas to hydrocarbons, producing mainly methane (see, for example, R. B. Anderson, *The Fischer-Tropsch Synthesis*, Academic Press (1984), p. 2). Iron and cobalt are able to produce higher chain hydrocarbons and are, thus, preferred as catalysts for the production of liquid hydrocarbons. However, other metals are also capable of catalyzing the conversion of synthesis gas. Among the Group VIII metals, ruthenium is a very active catalyst for the formation of hydrocarbons from syngas. Its activity at low temperatures is higher than that of Fe, Co, or Ni, and it produces a large amount of heavy hydrocarbons. At high pressures, it produces a large amount of high molecular weight waxes. Other metals which are highly active, such as rhodium, yield high amounts of oxygenated materials (see Ichikawa, Chemtech, 6, 74 (1982)). Osmium has been found to be moderately active, while Pt, Pd, and Ir exhibit low activity (see Pichler, *Advances in Catalysis*, vol. IV, Academic Press, N.Y. (1952), R. B. Anderson, *The Fischer-Tropsch Synthesis*, supra and Vannice, Journal of Catalysis, 50, 228–236).

Other metals that have been investigated include rhenium, molybdenum, and chromium, but these exhibit very low activity with most of the product being methane (see R. B. Anderson, *The Fischer-Tropsch Synthesis*, supra).

Various combinations of metals can also be used in the F-T process. Doping cobalt catalysts with nickel causes an increase in methane production during F-T synthesis (see *Catalysis*, vol. IV, Reinhold Publishing Co., (1956), p. 29). In U.S. Pat. No. 4,088,671 to T. P. Kobylinski, entitled "Conversion of Synthesis Gas Using a Cobalt-Ruthenium Catalyst", the addition of small amounts of ruthenium to cobalt is shown to result in a higher overall activity and lower methane production during F-T synthesis than using cobalt alone. Thus, these references teach that combinations of two or more F-T active metals can result in an active F-T catalyst with characteristics which are similar to the combined characteristics of each of the individual components.

Combinations of cobalt with non-F-T active metals have also been reported for the conversion of synthesis gas to specific products and, in some cases, at specific conditions. In Nakaoji, U.S. Pat. No. 3,988,344, the combination of cobalt with a second Group VIII metal and tungsten is claimed for the enhanced production of methane from synthesis gas. Knifton, U.S. Pat. No. 4,390,734 and Japanese Kokai 57/130932 describe the combination of Co and Rh for the production of oxygenated products, such as glycols or aldehydes. Fischer-Tropsch catalysts consisting of combinations of cobalt with either platinum or palladium, supported on a variety of solids, including alumina, have been reported by Sapienza et al., U.S. Pat. No. 4,396,539. These catalysts, however, relied on preparation from the metal carbonyls in order to form solid solutions on the surface of the solid support and were distinguished by an x-ray impermeable layer covering the support, thereby resulting in a catalyst exhibiting a unique x-ray diffraction pattern in which the structure of the solid support was completely masked by the metallic components. In particular, when the catalysts of the Sapienza et al. patent are supported on alumina, they are distinguished by the complete absence of any x-ray diffraction peaks in the $2\theta$ range of 65 to 70 degrees. In x-ray diffraction $\theta$ equals the angle of refraction.

Combinations of metals with certain oxide supports have also been reported to result in improved hydrocarbon yields during F-T synthesis. The use of titania to support cobalt or cobalt-thoria is taught in Payne et al., U.S. Pat. No. 4,595,703, entitles "Hydrocarbons from Synthesis Gas". In this case the support served to increase the activity of the metal(s) toward hydrocarbon formation. In fact, titania belongs to a class of metal oxides known to exhibit strong metal-support interactions and, as such, has been reported to give improved activity for a number of metals during F-T synthesis (see for example, M. A. Vannice, Journal of Catalysis, 74, 199 (1982)). Combinations of titania and two or more metals have also been shown to yield improved F-T activity. In Mauldin, U.S. Pat. No. 4,568,663, the use of combinations of cobalt and rhenium, or cobalt, rhenium, and thoria, supported on titania is claimed as useful for the production of hydrocarbons from methanol or synthesis gas.

In a series of European patent applications (EP 110449, EP 142888, EP 167215, and EP 188304), Shell International described an improved F-T catalyst comprised of cobalt promoted by at least one of the metals in the group consisting of zirconium, titanium, and chromium, preferably supported on silica, alumina, or silica-alumina. The addition of Group VIII noble metals to zirconia-promoted cobalt catalysts was claimed in European patent application EP 221598, which teaches improved activity upon addition of platinum to a cobalt catalyst already promoted with zirconia. Thus, the Shell work shows that the addition of a Group VIII metal to a Fischer-Tropsch catalyst is only useful when the catalyst already incorporates a well known promoter, such as zirconia, as a main component of the catalyst.

SUMMARY OF THE INVENTION

We have found, unexpectedly, that the addition of platinum, iridium, or rhodium to a cobalt catalyst supported on an alumina carrier results in a significant increase in activity for the conversion of synthesis gas to hydrocarbons, even in the absence of additional metal or metal oxide promoters. The surprising feature of this invention is that the improvement in activity is much higher than would be expected from the combination of the individual components, especially in light of the facts that (1) the metals platinum, iridium, and rhodium are not very active F-T catalysts, (2) the combination of cobalt and alumina does not in itself result in a significant increase in F-T synthesis activity compared to cobalt on other supports, and (3) no increase in methane or oxygenate production is observed upon addition of the second metal to cobalt despite the fact that the main product in the conversion of syngas over platinum or iridium is methane and over rhodium is oxygenates.

It has been found in accordance with the present invention that synthesis gas comprising hydrogen and carbon monoxide can be converted to liquid hydrocarbons by using a process which includes the step of contacting such a synthesis gas feed over a catalyst comprising amounts of cobalt catalytically active in a Fischer-Tropsch Synthesis and at least one loading-insensitive second metal selected from the group consisting of platinum, iridium, and rhodium composited on an alumina support. The a finished catalyst exhibits a positive x-ray diffraction pattern having peaks in the $2\theta$ range of about 65 to 70 degrees, where $\theta$ is the angle of refraction. The second metal is present in relatively lesser amounts than the cobalt content. The catalyst preferably contains from about 5 to 60 wt % cobalt and has a content of the second metal between about 0.1 and 50 wt % of the cobalt content of the catalyst. The alumina preferably is gamma alumina.

It has been found that the addition of one or more of the metals from the group consisting of platinum, iridium, and rhodium to a catalyst consisting predominantly of cobalt supported on alumina results in greatly enhanced activity for the conversion of synthesis gas to hydrocarbons. Platinum, iridium, and rhodium are not very active as Fischer-Tropsch catalysts on their own, and it has surprisingly been found that the addition of the other non-Fischer-Tropsch noble metals to a cobalt catalyst does not result in greatly improved activity. The improvement upon addition of platinum, iridium, or rhodium to a cobalt catalyst is surprisingly not observed when the catalytic components are distended on supports other than alumina, for example silica or titania.

BRIEF DESCRIPTION OF THE FIGURES

The present invention will be understood better by reference to the Figures in which.

DETAILED DESCRIPTION OF THE PREFERRED EMBODIMENTS

Figure 1:
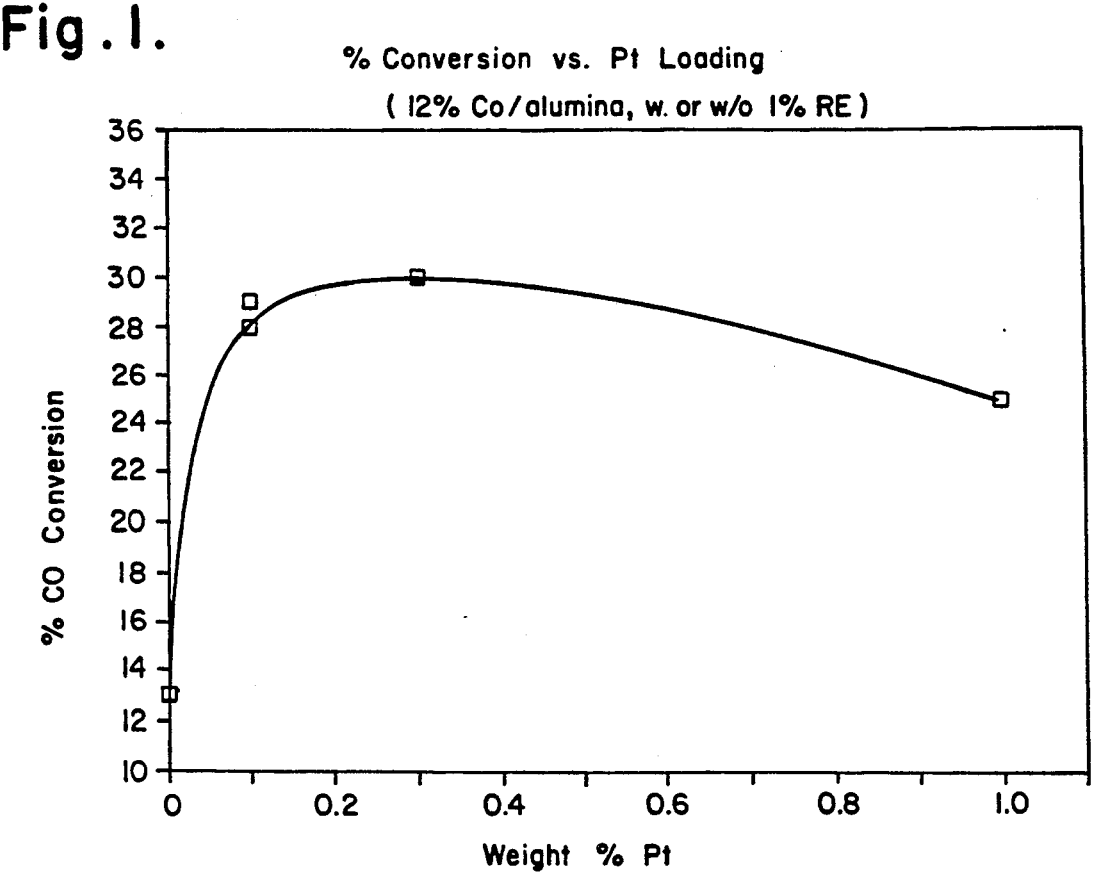
FIG. 1 is a graph showing carbon monoxide conversion versus platinum content for alumina supported catalysts containing cobalt plus platinum.

The catalyst used in the process of the present invention comprises as the active catalytic ingredients cobalt and one or more metals from the group consisting of platinum, iridium, and rhodium supported on alumina with the second metal present in a relatively smaller amount than cobalt. The finished catalyst exhibits a positive x-ray diffraction pattern having peaks in the $2\theta$ range of about 65 to 70 degrees. This catalyst has been found to be highly active for the conversion of synthesis gas, a mixture of hydrogen and carbon monoxide, into a mixture of predominately paraffinic hydrocarbons. As indicated above, it has long been known that cobalt is an active catalyst for the F-T synthesis. It is also known that the addition of ruthenium to a cobalt catalyst gives improved activity, but ruthenium is known to be an active Fischer-Tropsch metal on its own. In our invention, it has been found that among the non-Fischer-Tropsch metals in Group VIII of the Periodic Table, some of these metals produce enhanced activity when added to a supported cobalt catalyst without the need to form solid solutions on the surface of the support, while others of these metals give no improvement. Although a number of supports have been studied in the present work and the improvement of this invention has only been observed with alumina, the discovery of another support exhibiting a similar effect would not be entirely surprising.

The cobalt is added to the alumina support in some amount up to about 60 wt % of the catalyst, including cobalt. Preferably, amounts between about 5 and 45 wt % are used; and more preferably between about 10 and 45 wt %. The content of platinum and/or iridium and/or rhodium is between about 0.1 and 50 wt % of the cobalt content; preferably between about 0.1 and 30 wt %; and more preferably from about 0.5 to around 20 wt %.

In addition to cobalt and one or more metals from the group consisting of platinum, iridium and rhodium, it is beneficial to include a small amount of a metal oxide promoter in an amount between about 0.1 and 5 wt %, and more preferably between about 0.2 and 2 wt %, based on the weight of the complete catalyst. The promoter is suitably chosen from elements in groups IIIB, IVB and VB of the periodic chart, the lanthanides and actinides. The promoter oxide can be chosen from, for example, $Sc_2O_3$, $Y_2O_3$, $La_2O_3$, $Ce_2O_3$, $Pr_2O_3$, $Ac_2O_3$, $PaO_2$, $Nd_2O_2$, $CeO_2$, $V_2O_5$ or $Nb_2O_5$. The most preferable oxide is $La_2O_3$, or a mixture of lanthanides, rich in lanthanum. Oxides like MnO or MgO can also be included. While not essential, the use of these metal oxides is common in the art, since they are believed to promote the production of products with higher boiling points, while maintaining or improving catalytic activity. However, the catalyst is highly active and selective without the addition of a promoter.

THE CATALYST SUPPORT

The catalytically active metals and the promoter metal oxide, if present, are distended on alumina. Although other supports may be used, it has been found, for example, that silica and titania produce catalysts with much lower activities that show no, or only slight, improvement upon addition of one or more metals from the group consisting of platinum, iridium, and rhodium.

To be most effective when used as a support, alumina should be characterized by low acidity, high surface area, and high purity. These properties are necessary in order to enable the catalyst to have a high activity and exhibit a low deactivation rate and to produce high molecular weight hydrocarbon products. The surface area of the alumina support is at least about 100 $m^2/g$; and more preferably at least about 150 $m^2/g$. The pore volume is at least, and preferably greater than, about 0.3 $cm^3/g$. The catalyst support must be of high purity. That is, the content of elements, e.g. sulfur and phosphorous, that have a deleterious effect on the catalyst support should be kept below 100 ppm and preferably below 50 ppm. Although gamma alumina has generally been used and is preferred, a number of alumina structures, if prepared properly, can meet these conditions and are suitable supports. For example, eta-alumina, xi-alumina, theta-alumina, delta-alumina, kappa-alumina, boehmite, and pseudo-boehmite can all be used as supports.

CATALYST PREPARATION

The method of depositing the active metals and the promoter oxide on the alumina support is not critical, and can be chosen from various methods well known to those skilled in the art. One suitable method that has been employed is known as incipient wetness impregnation. In this method the metal salts are dissolved in an amount of a suitable solvent just sufficient to fill the pores of the catalyst. In another method, the metal oxides or hydroxides are coprecipitated from an aqueous solution by adding a precipitating agent. In still another method, the metal salts are mixed with the wet support in a suitable blender to obtain a substantially homogeneous mixture. In the present invention, if incipient wetness impregnation is used, the catalytically active metals can be deposited on the support using an aqueous or an organic solution. Suitable organic solvents include, for example, acetone, methanol, ethanol, dimethyl formamide, diethyl ether, cyclohexane, xylene, and tetrahydrofuran. Aqueous impregnation is preferred when $Co(NO_3)_2$ is used as the salt.

Suitable cobalt compounds include, for example, the cobalt salts, cobalt nitrate, cobalt acetate and cobalt chloride, with the nitrate being the most preferable when impregnating from an aqueous solution. Suitable platinum, iridium, and rhodium compounds include, for example, the nitrates, chlorides, and complexes with ammonia. The promoter can suitably be incorporated into the catalyst in the form, for example, of the nitrate or chloride.

After aqueous impregnation, the catalyst is dried at 110° to 120° C. for 3 to 6 hours. When impregnating from organic solvents, the catalyst is preferably first dried in a rotary evaporator apparatus at 50° to 60° C. under low pressure, then dried at 110° to 120° C. for several hours longer.

The dried catalyst is calcined under flowing air by slowly increasing the temperature to an upper limit of between 200° and 500° C., preferably between 250° and 350° C. The rate of temperature increase is preferably between 0.5° and 2° C. per minute, and the catalyst is held at the highest temperature for a period of 2 to 3 hours. The impregnation procedure is repeated as many times as necessary to obtain a catalyst with the desired metals content. Cobalt and platinum, iridium, or rhodium and the promoter, if present, can be impregnated together, or in separate steps. If separate steps are used, the order of impregnating the active components can be varied.

Before use, the calcined catalyst is reduced with hydrogen. This can suitably be done in flowing hydrogen at atmospheric pressure at a flow rate between 30 and 100 $cm^3/min$ when reducing about 2 g of catalyst. The flow rate should suitably be increased for larger quantities of catalyst. The temperature is increased at a rate between 0.5° and 2° C. per minute from ambient to a maximum level of 250° to 450° C., preferably between 300° and 400° C., and maintained at the maximum temperature for about 6 to 24 hours, more preferably 10 to 24 hours.

The reduced catalysts of the present invention are characterized by exhibiting the distinguishing x-ray diffraction pattern of alumina. In particular, the presence of x-ray diffraction peaks in the 2 $\theta$ range of 65 to 70 degrees clearly indicates the absence of any solid solution covering the surface of the support as taught by Sapienza et al. in U.S. Pat. No. 4,396,539 discussed above, and clearly distinguishes the catalysts of the present invention from those described by the Sapienza et al. patent.

Figure 8:
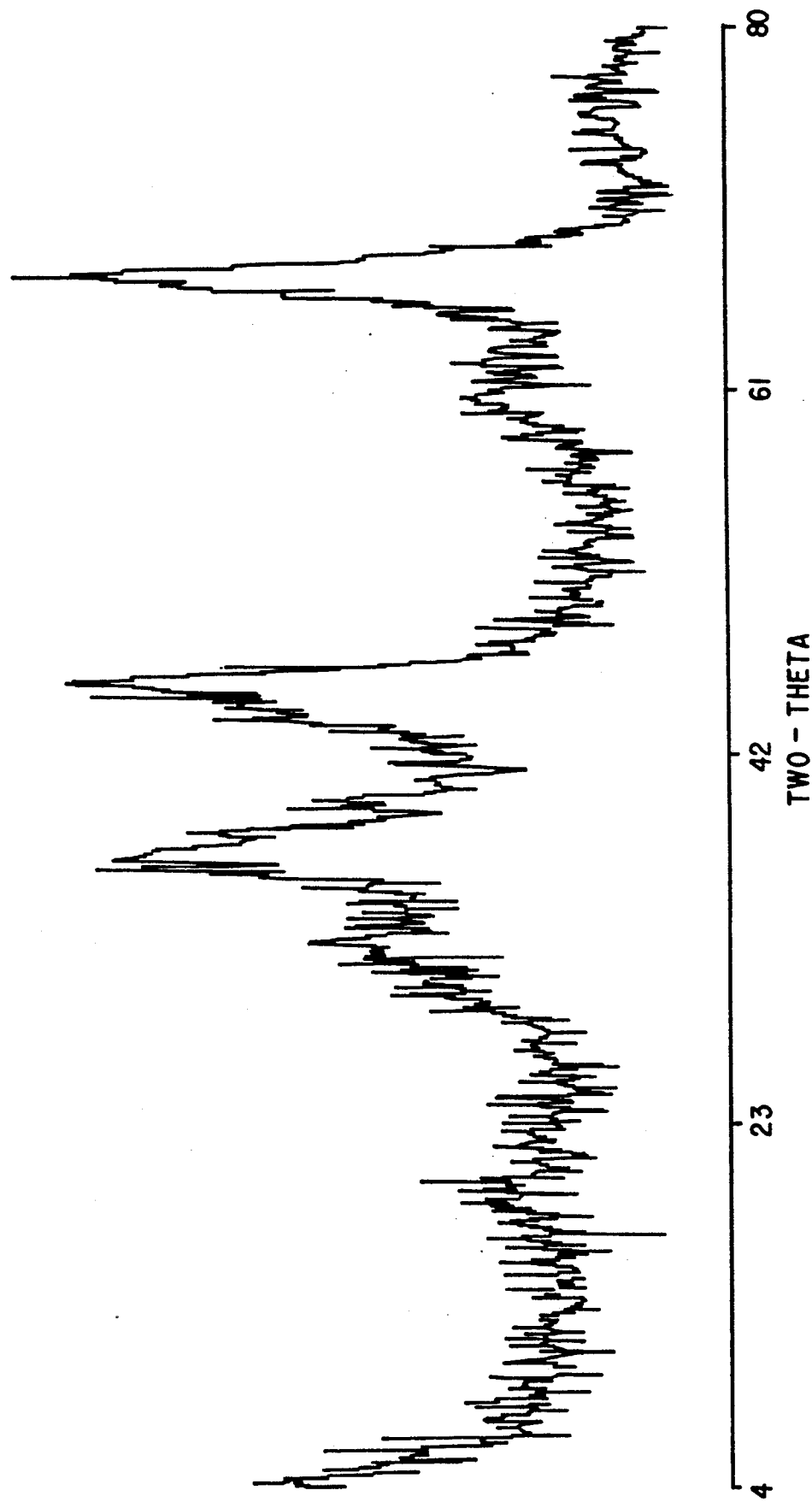
FIG. 8 is the x-ray diffraction pattern for a catalyst in accordance with this invention containing cobalt and platinum supported on alumina.
Figure 9:
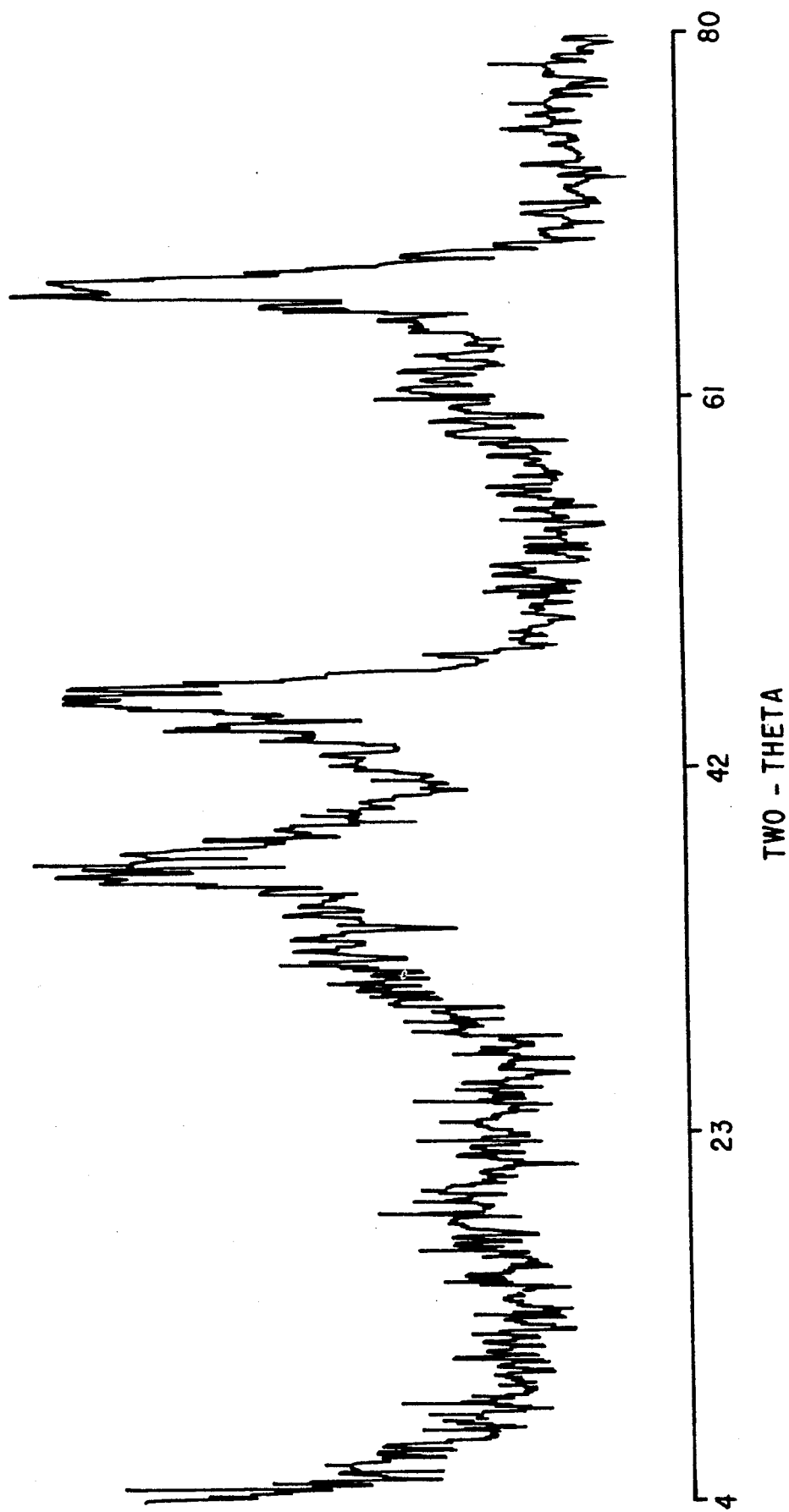
FIG. 9 is the x-ray diffraction pattern for a catalyst in accordance with this invention containing cobalt and rhodium supported on alumina.
Figure 10:
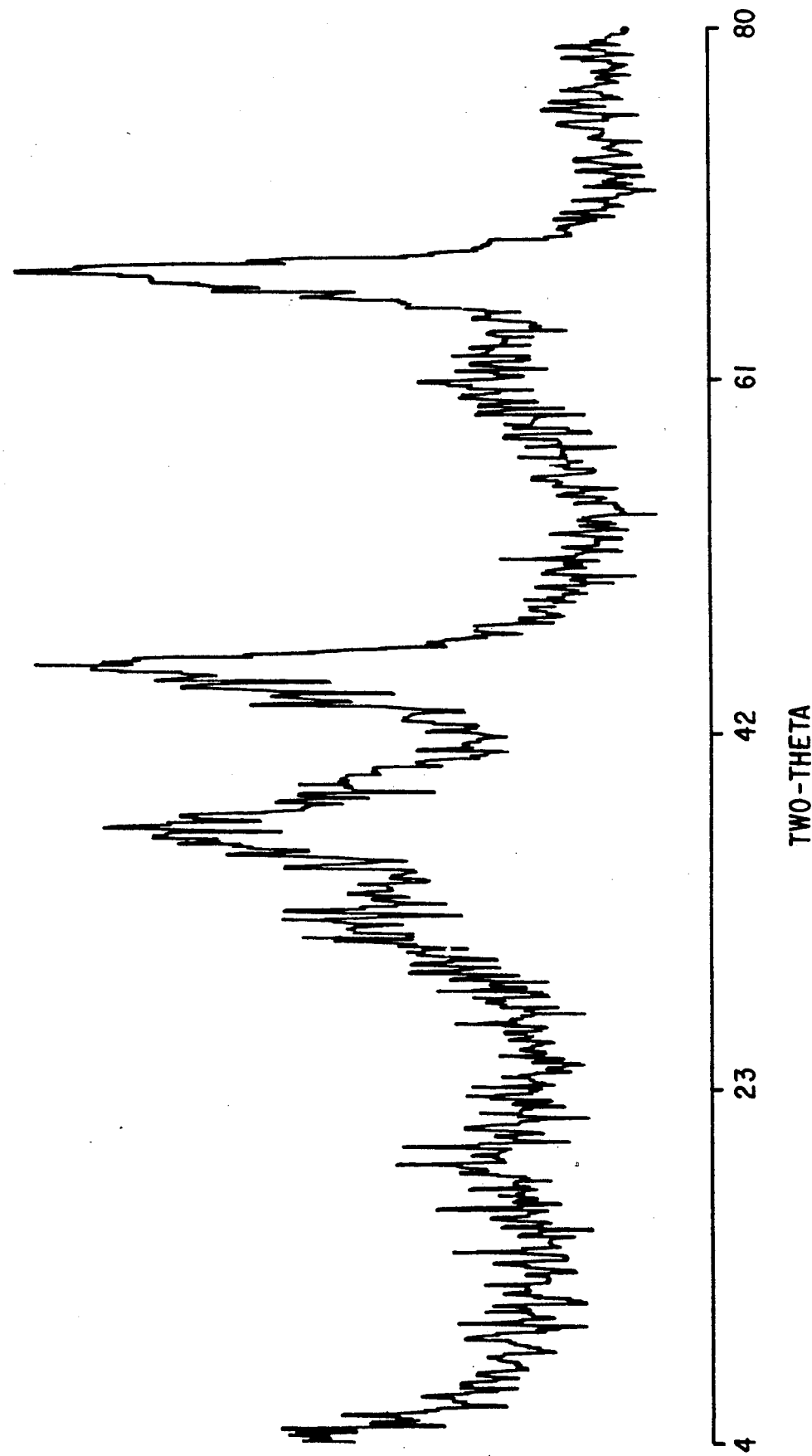
FIG. 10 is the x-ray diffraction pattern for a catalyst in accordance with this invention containing cobalt and iridium supported on alumina.

X-ray diffraction patterns of catalysts in accordance with the present invention are shown in FIGS. 8, 9 and 10. These x-ray diffraction patterns were obtained on the catalysts of Examples 6, 9 and 12, respectively. The catalysts were reduced and passivated before being submitted for x-ray diffraction analysis.

After the reduction step, the catalysts may be oxidized and rereduced before use. To carry out the oxidation step, the catalyst is treated with dilute oxygen (1–3% oxygen in nitrogen) at room temperature for a period of ½ to 2 hours before the temperature is increased at the same rate and to the same temperature as used during calcination. After holding the highest temperature for 1 to 2 hours, air is slowly introduced, and the treatment is continued under air at the highest temperature for another 2 to 4 hours. The second reduction is carried out under the same conditions as the first reduction.

HYDROCARBON SYNTHESIS

The reactor used for the synthesis of hydrocarbons from synthesis gas can be chosen from various types well known to those skilled in the art, for example, fixed bed, fluidized bed, ebullating bed or slurry. The catalyst particle size for the fixed or ebullating bed is preferably between 0.1 and 10 mm and more preferably between 0.5 and 5 mm. For the other types of operations a particle size between 0.01 and 0.2 mm is preferred.

The synthesis gas is a mixture of carbon monoxide and hydrogen and can be obtained from any source known to those skilled in the art, such as, for example, steam reforming of natural gas or partial oxidation of coal. The molar ratio of $H_2:CO$ is preferably between 1:1 to 3:1; and more preferably between 1.5:1 to 2.5:1. Carbon dioxide is not a desired feed component for use with the catalyst of this invention, but it does not adversely affect the activity of the catalyst. All sulfur compounds must, on the other hand, be held to very low levels in the feed, preferably below 1 ppm.

The reaction temperature is suitably between 150° and 300° C.; and more preferably between 175° and 250° C. The total pressure can be from atmospheric to around 100 atmospheres, preferably between 1 and 30 atmospheres. The gaseous hourly space velocity, based on the total amount of synthesis gas feed, is preferably between 100 and 20,000 $cm^3$ of gas per gram of catalyst per hour; and more preferably from 1000 to 10,000 $cm^3/g/h$, where gaseous hourly space velocity is defined as the volume of gas (measured at standard temperature and pressure) fed per unit weight of catalyst per hour.

The reaction products are a complicated mixture, but the main reaction can be illustrated by the following equation:

$$nCO + 2nH_2 \rightarrow (-CH_2-)_n + nH_2O$$

where $(-CH_2-)_n$ represents a straight chain hydrocarbon of carbon number n. Carbon number refers to the number of carbon atoms making up the main skeleton of the molecule. In F-T synthesis, the products are generally either paraffins, olefins, or alcohols. Products range in carbon number from one to 50 or higher.

In addition, with many catalysts, for example those based on iron, the water gas shift reaction is a well known side reaction:

$$CO + H_2O \rightarrow H_2 + CO_2$$

With cobalt catalysts the rate of this last reaction is usually very low. The same low rate of the water gas shift reaction is observed with catalysts containing platinum, iridium, or rhodium in addition to cobalt.

The hydrocarbon products from Fischer-Tropsch synthesis are distributed from methane to high boiling compounds according to the so called Schulz-Flory distribution, well known to those skilled in the art. The Schulz-Flory distribution is expressed mathematically by the Schulz-Flory equation:

$$W_i = (1-\alpha)^2 i \alpha^{i-1}$$

where i represents carbon number, $\alpha$ is the Schulz-Flory distribution factor which represents the ratio of the rate of chain propagation to the rate of chain propagation plus the rate of chain termination, and $W_i$ represents the weight fraction of product of carbon number i.

The products produced by the catalyst of this invention generally follow the Schulz-Flory distribution, except that the yield of methane is usually higher than expected from this distribution. This indicates that methane is apparently produced by an additional mechanism.

It is well known, and also shown in the following examples, that the metals from the group consisting of platinum, iridium, and rhodium are alone low activity catalysts for Fischer-Tropsch synthesis producing products which are predominantly methane, or in the case of rhodium, oxygenates.

The catalyst of this invention is further described in the following examples.

EXPERIMENTAL WORK

The following examples describe the preparation of various catalysts and the results obtained from testing these catalysts for conversion of synthesis gas into hydrocarbons.

Before being tested, each catalyst was given a pretreatment consisting of reduction by passing hydrogen over the catalyst at a rate of 3000 $cm^3/g/h$ while heating the catalyst at a rate of 1° C./min to 350° C. and maintaining this temperature for 10 hours. In the tests, synthesis gas consisting of 33 vol % carbon monoxide and 67 vol % hydrogen was passed over 0.5 g of the catalyst at atmospheric pressure at temperatures of 185°, 195° and 205° C. according to the following schedule:

9 hr. 50 min. at 195° C.
4 hr. 20 min. at 205° C.
4 hr. 30 min. at 185° C.
9 hr. 50 min. at 195° C.

The flow rate of synthesis gas was 1680 $cm^3/g$ of catalyst/h. Products from the reactor were sent to a gas chromatograph for analysis. Catalysts were compared based on the results over the period from 10 to 30 hours on stream.

EXAMPLE 1

Catalyst Containing Cobalt but No Second Metal

This example describes the preparation of a control cobalt catalyst which was used for comparative purposes. This catalyst was prepared as follows:

A solution was prepared by dissolving 17.03 g of cobalt nitrate, $Co(NO_3)_2 \cdot 6H_2O$, and 0.76 g of mixed rare earth nitrate, $RE(NO_3)_3$, where RE stands for rare earth with a composition of 66% $La_2O_3$, 24% $Nd_2O_3$, 8.2% $Pr_6O_{11}$, 0.7% $CeO_2$, and 1.1% other oxides (Molycorp 5247), in 30 ml of distilled water. The total solution was added with stirring to 25 g of Ketjen CK300 gamma-alumina, which had been calcined 10 hours at 500° C. The prepared catalyst was then dried for 5 hours in an oven at a temperature of 115° C. The dried catalyst was then calcined in air by raising its temperature at a heating rate of 1° C./minute to 300° C. and holding at this temperature for 2 hours. The finished catalyst contained 12 wt % cobalt and 1 wt % rare earth oxide with the remainder being alumina. This catalyst is referred to as preparation "a" in Table I. The above procedure was repeated to produce the preparation "b" catalyst in Table I.

The results of the tests with this catalyst are shown in Table I. In this and the following table, selectivity is defined as the percent of the carbon monoxide converted that goes to the indicated product.

TABLE I

| Temp. °C. | Prep. | CO Conversion % | $C_2+$ Selectivity % | $CH_4$ Selectivity % | $CO_2$ Selectivity % |
|---|---|---|---|---|---|
| 185 | a | 7 | 91.2 | 7.1 | 1.7 |
| | b | 11 | 91.9 | 7.0 | 1.1 |
| 195 | a | 12 | 90.1 | 8.8 | 1.1 |
| | b | 18 | 90.3 | 8.9 | 0.8 |
| 205 | a | 21 | 87.8 | 11.2 | 1.0 |

TABLE I-continued

| Temp. °C. | Prep. | CO Conversion % | $C_2+$ Selectivity % | $CH_4$ Selectivity % | $CO_2$ Selectivity % |
|---|---|---|---|---|---|
| | b | 29 | 86.8 | 12.3 | 0.9 |

This example shows that a cobalt catalyst exhibits good selectivity to ethane and longer chain length hydrocarbons and low selectivity to methane and carbon dioxide.

EXAMPLE 2, 3, 4

Catalysts Containing Pt, Ir, or Rh, but No Cobalt

The preparation procedure of Example 1 was employed to prepare catalysts containing 1 wt % Pt, 1 wt % Ir, and 1 wt % Rh, but without cobalt. When these catalysts were tested (see Table II), they showed very low activities, as expected, since Pt, Ir, and Rh are known to be two to three orders of magnitude less active than Co (see, for example, M. A. Vannice, Journal of Catalysis, vol. 50, pp. 228–236).

TABLE II

| Example No. | Cobalt wt % | Second Metal Type | Second Metal wt % | CO conv. % | $C_2+$ sel. % | $CH_4$ sel. % | $CO_2$ sel. % |
|---|---|---|---|---|---|---|---|
| 2 | 0 | Pt | 1.0 | <1 | 11.2 | 47.7 | 41.1 |
| 3 | 0 | Ir | 1.0 | <1 | 12.4 | 47.4 | 40.2 |
| 4 | 0 | Rh | 1.0 | <1 | 12.8 | 50.4 | 36.8 |

All catalysts included 1% rare earth oxides.

It is obvious from the results in Table II that the high activities of the catalysts of this invention are not due to an additive effect of catalytic components, but must be due to some more complex interaction.

EXAMPLES 5 THROUGH 14

Catalysts Containing Cobalt and Platinum, Iridium or Rhodium

The preparation procedure of Example 1 was employed, except that varying amounts of tetrammine platinum dinitrate, iridium trichloride, or rhodium dinitrate were added to the solution.

The results of catalysts containing 12% cobalt and different amounts of Pt, Ir, or Rh are shown in Table III. The test was run as described above.

TABLE III

| Example No. | Cobalt wt % | Second Metal Type | Second Metal wt % | CO conv. % | $C_2+$ sel. % | $CH_4$ sel. % | $CO_2$ sel. % |
|---|---|---|---|---|---|---|---|
| 5 | 12 | Pt | 0.1 | 28 | 90.1 | 9.4 | 0.5 |
| 6 | 12 | Pt | 0.1 | 29 | 89.3 | 10.0 | 0.7 |
| 7 | 12 | Pt | 0.3 | 30 | 88.7 | 10.5 | 0.8 |
| 8 | 12 | Pt | 1.0 | 25 | 88.3 | 10.5 | 1.2 |
| 9 | 12 | Ir | 0.1 | 30 | 89.5 | 9.7 | 0.8 |
| 10 | 12 | Ir | 0.3 | 31 | 89.1 | 9.9 | 1.0 |
| 11 | 12 | Ir | 1.0 | 31 | 89.1 | 9.9 | 1.0 |
| 12 | 12 | Rh | 0.1 | 27 | 88.0 | 11.0 | 1.0 |
| 13 | 12 | Rh | 0.3 | 27 | 89.0 | 10.2 | 0.8 |
| 14 | 12 | Rh | 1.0 | 25 | 88.5 | 10.8 | 0.7 |

All catalysts included 1% rare earth oxides, except for example 5 which did not include rare earth oxides.

By comparing the results in Tables I and III, it is seen that the catalytic activity is clearly improved upon addition of Pt, Ir, or Rh to a Co catalyst. Catalytic activity reaches a maximum level with only 0.1% of the second metal present.

EXAMPLES 15 THROUGH 22

Catalysts Containing Cobalt and Platinum, Iridium, or Rhodium

These catalysts were prepared as in Examples 1 and 5 to 14, giving catalysts with different amounts of cobalt and different amounts of platinum, iridium, or rhodium, plus 1 wt % rare earth oxides.

The results of catalysts with 20% Co and 0.17% Pt, Ir, or Rh and 40% Co and 0.33% Pt, Ir, or Rh are shown in Table IV. For comparision, the results for catalysts with 20 and 40% cobalt without any second metal are included in Table IV. The results are also shown in FIGS. 4, 5, and 6.

TABLE IV

| Example No. | Cobalt wt % | Second Metal Type | Second Metal wt % | CO conv. % | $C_2+$ sel. % | $CH_4$ sel. % | $CO_2$ sel. % |
|---|---|---|---|---|---|---|---|
| 15 | 20 | — | — | 20 | 89.4 | 9.7 | 0.9 |
| 16 | 20 | Pt | 0.17 | 40 | 85.9 | 12.9 | 1.2 |
| 17 | 20 | Ir | 0.17 | 41 | 86.5 | 12.2 | 1.3 |
| 18 | 20 | Rh | 0.17 | 42 | 87.0 | 12.0 | 1.0 |
| 19 | 40 | — | — | 20 | 89.4 | 9.6 | 1.0 |
| 20 | 40 | Pt | 0.33 | 53 | 83.1 | 14.7 | 2.2 |
| 21 | 40 | Ir | 0.33 | 53 | 84.0 | 13.8 | 2.2 |
| 22 | 40 | Rh | 0.33 | 53 | 83.2 | 14.7 | 2.1 |

Figure 4:
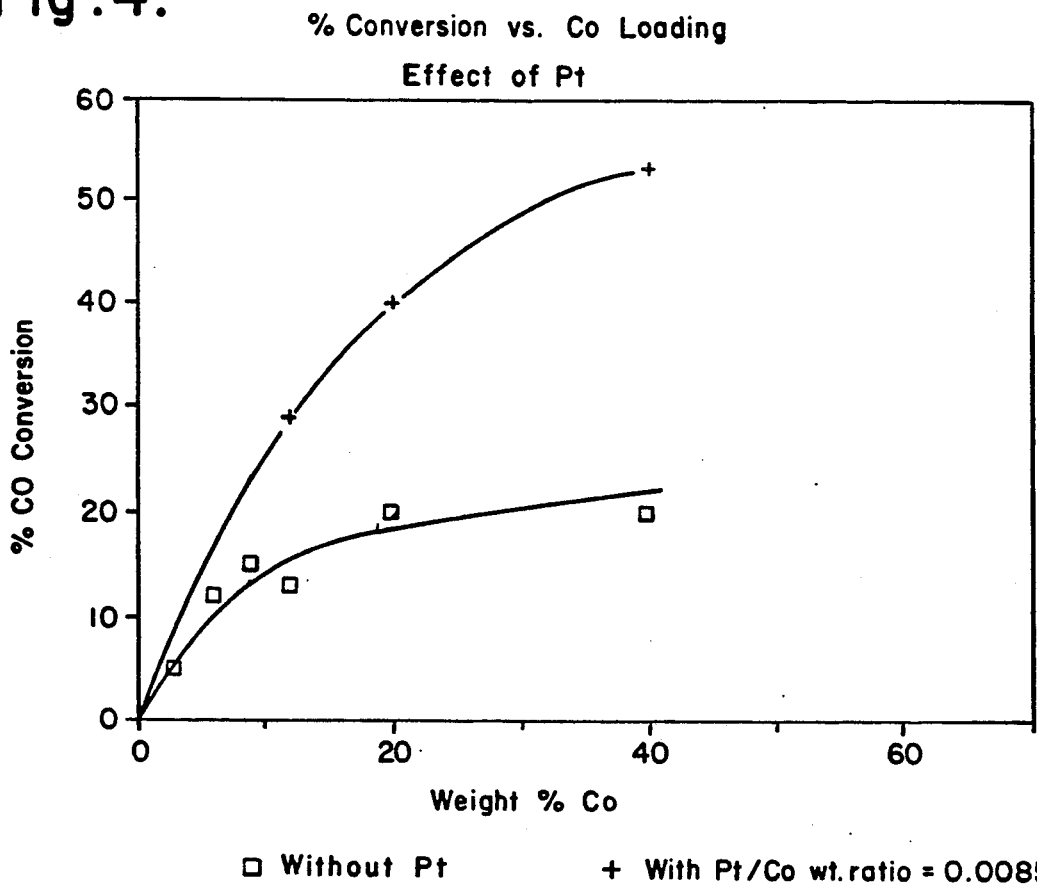
FIG. 4 is a graph showing carbon monoxide conversion versus cobalt content for alumina supported catalysts containing only cobalt and for catalysts containing cobalt plus platinum.
Figure 5:
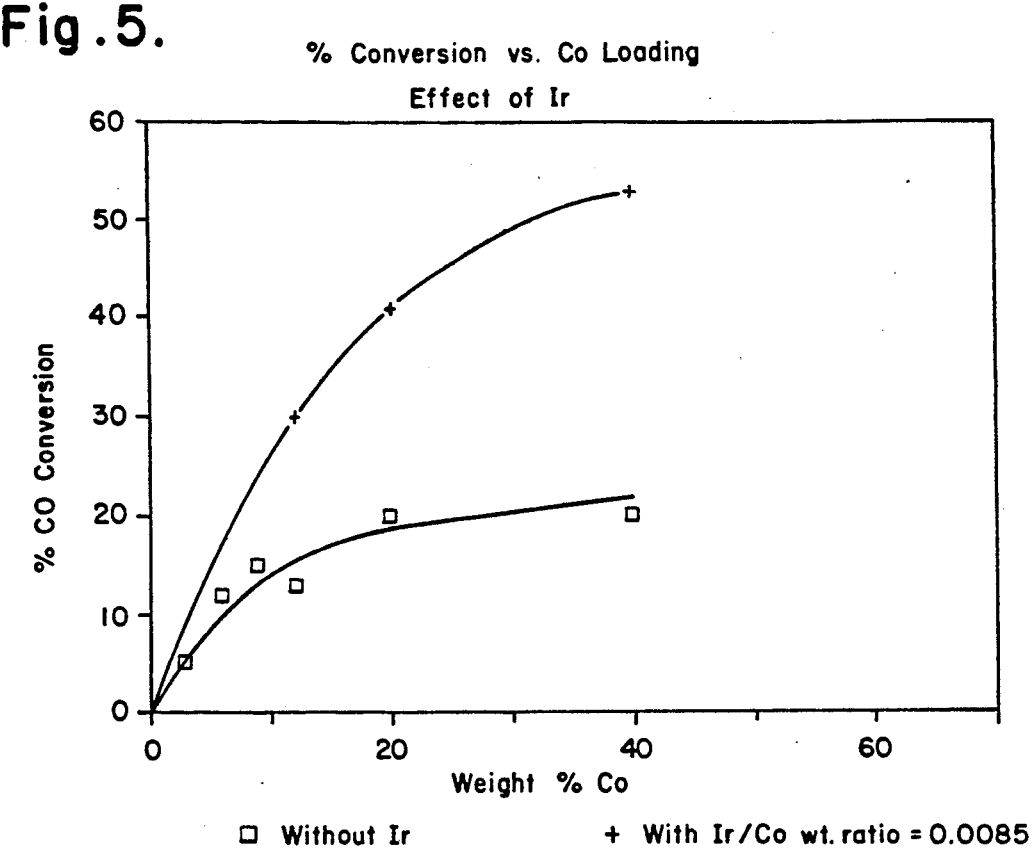
FIG. 5 is a graph showing carbon monoxide conversion versus cobalt content for alumina supported catalysts containing only cobalt and for catalysts containing cobalt plus iridium.
Figure 6:
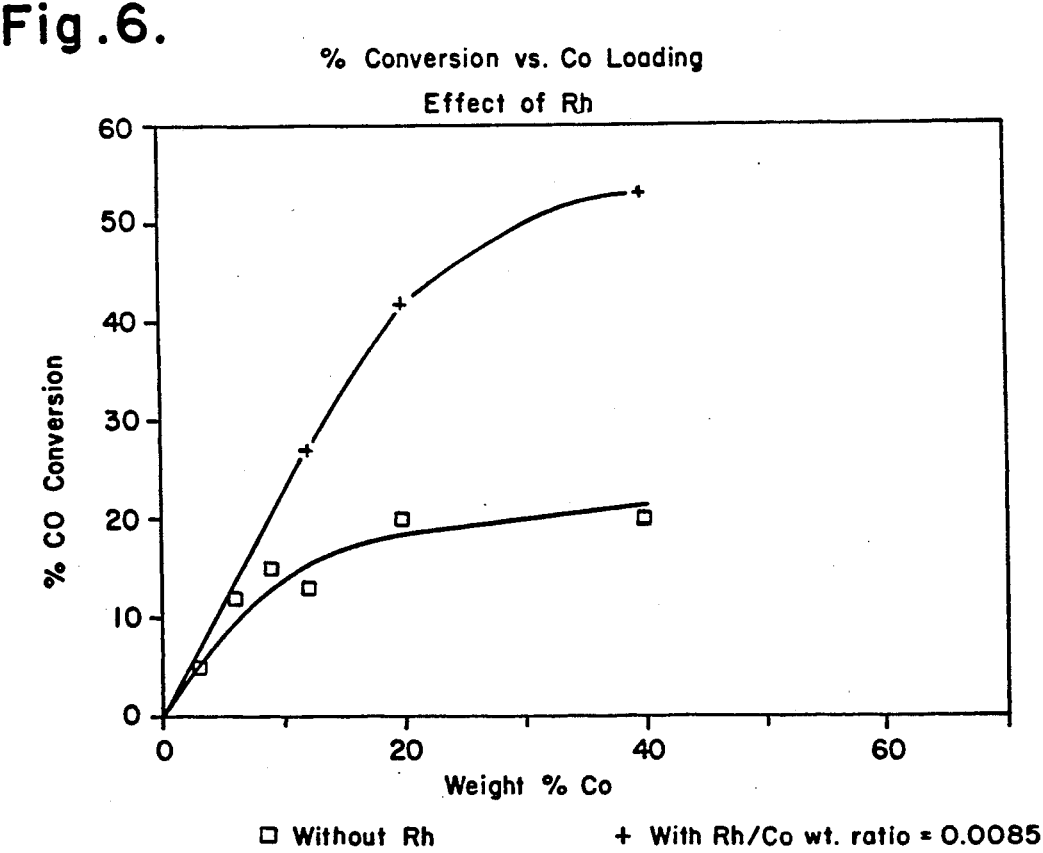
FIG. 6 is a graph showing carbon monoxide conversion versus cobalt content for alumina supported catalysts containing only cobalt and for catalysts containing cobalt plus rhodium.

The results in Table IV and FIGS. 4, 5, and 6 show that the improvement upon addition of Pt, Ir, or Rh to a Co catalyst is even more pronounced at a high Co loading.

EXAMPLES 23 THROUGH 25

Catalysts Containing Cobalt and Combinations of Platinum, Rhodium, or Iridium

The catalysts were prepared as described in Example 1, with addition of two of the three metal salts: tetrammine platinum dinitrate, iridium trichloride, or rhodium dinitrate.

The results from tests with catalysts containing 12 wt % cobalt and two of the three metals Pt, Ir, or Rh are shown in Table V.

TABLE V

| Example No. | Cobalt wt % | Second Metal Type | Second Metal wt % | CO conv. % | $C_2+$ sel. % | $CH_4$ sel. % | $CO_2$ sel. % |
|---|---|---|---|---|---|---|---|
| 23 | 12 | Pt | 0.05 | 25 | 87.4 | 12.6 | 1.1 |
|    |    | Ir | 0.05 |    |      |      |     |
| 24 | 12 | Ir | 0.05 | 26 | 86.8 | 13.2 | 1.2 |
|    |    | Rh | 0.05 |    |      |      |     |
| 25 | 12 | Pt | 0.05 | 26 | 86.8 | 13.2 | 1.3 |
|    |    | Rh | 0.05 |    |      |      |     |

The results in Table V show that adding a combination of second metals chosen from the group consisting of Pt, Ir, and Rh to a cobalt on alumina catalyst produces the same improvement in catalytic activity as achieved by adding only one of these second metals. This means that the desired loading of second metal on the catalyst can be made up of any desired combination of Pt, Ir, and Rh.

EXAMPLES 26 THROUGH 35

Catalysts Containing Cobalt and Platinum, Iridium, or Rhodium Supported on Supports Other Than Alumina The catalysts were prepared as described in Example 1, with addition of Pt, Ir, or Rh salts. In these examples, $SiO_2$ (Grade 59 from Davison Chemicals) and $TiO_2$ (P25 from Degussa) were used as supports.

The results from these tests are shown in Table VI. For comparison, the table includes the results for catalysts without Pt, Ir, or Rh supported on $SiO_2$ and $TiO_2$.

TABLE VI

| Example No. | Cobalt wt % | Second Metal Type | Second Metal wt % | CO conv. % | $C_2+$ sel. % | $CH_4$ sel. % | $CO_2$ sel. % |
|---|---|---|---|---|---|---|---|
| | | Silica Support | | | | | |
| 26 | 12 | — | — | 11 | 90.2 | 8.6 | 1.2 |
| 27 | 12 | Pt | 0.1 | 12 | 89.1 | 9.1 | 1.8 |
| 28 | 12 | Pt | 1.0 | 14 | 89.0 | 9.0 | 2.0 |
| | | | | 12 | 86.1 | 11.1 | 2.8 |
| 29 | 12 | Ir | 0.1 | 13 | 90.8 | 7.7 | 1.5 |
| 30 | 12 | Rh | 0.1 | 11 | 90.0 | 8.0 | 2.0 |
| | | Titania Support | | | | | |
| 31 | 12 | — | — | 11 | 87.7 | 11.7 | 0.6 |
| 32 | 12 | Pt | 0.1 | 12 | 86.8 | 11.4 | 1.8 |
| 33 | 12 | Pt | 1.0 | 14 | 82.5 | 12.6 | 4.9 |
| | | | | 12 | 79.5 | 14.5 | 6.0 |
| 34 | 12 | Ir | 0.1 | 13 | 87.5 | 11.1 | 1.4 |
| 35 | 12 | Rh | 0.1 | 12 | 85.1 | 11.2 | 3.7 |

These results show that the improvement in activity observed upon addition of small amounts of Pt, Ir, or Rh to a cobalt catalyst supported on alumina is not observed when the support is either silica or titania.

EXAMPLES 36 THROUGH 40

Catalysts Containing Cobalt and Other Non-Fischer-Tropsch Metals from Group VIII These catalyst were prepared to illustrate the difference between cobalt catalysts containing Pt, Ir, or Rh and cobalt catalysts containing other, non-Fischer-Tropsch metals from Group VIII in the Periodic Table. The catalysts were prepared as explained in Example 1, except that different amounts of tetrammine palladium dinitrate, nickel dinitrate, or osmium trichloride were added.

The results from the tests of these catalysts are shown in Table VII.

TABLE VII

| Example No. | Cobalt wt % | Second Metal Type | Second Metal wt % | CO conv. % | $C_2+$ sel. % | $CH_4$ sel. % | $CO_2$ sel. % |
|---|---|---|---|---|---|---|---|
| 36 | 12 | Pd | 0.1 | 22 | 87.8 | 12.2 | 1.7 |
| 37 | 12 | Pd | 0.3 | 18 | 88.3 | 10.9 | 0.8 |
| 38 | 12 | Pd | 1.0 | 8 | 83.0 | 15.6 | 1.4 |
| 39 | 12 | Ni | 0.3 | 16 | 89.6 | 9.5 | 0.9 |
| 40 | 12 | Os | 1.0 | 18 | 90.2 | 9.0 | 0.8 |

The results show clearly that the improvement upon addition of Pt, Ir, or Rh to a cobalt catalyst is much more pronounced compared to the slight or no improvement upon addition of other, non-Fischer-Tropsch metals from Group VIII.

DISCUSSION OF EXAMPLES

Figure 2:
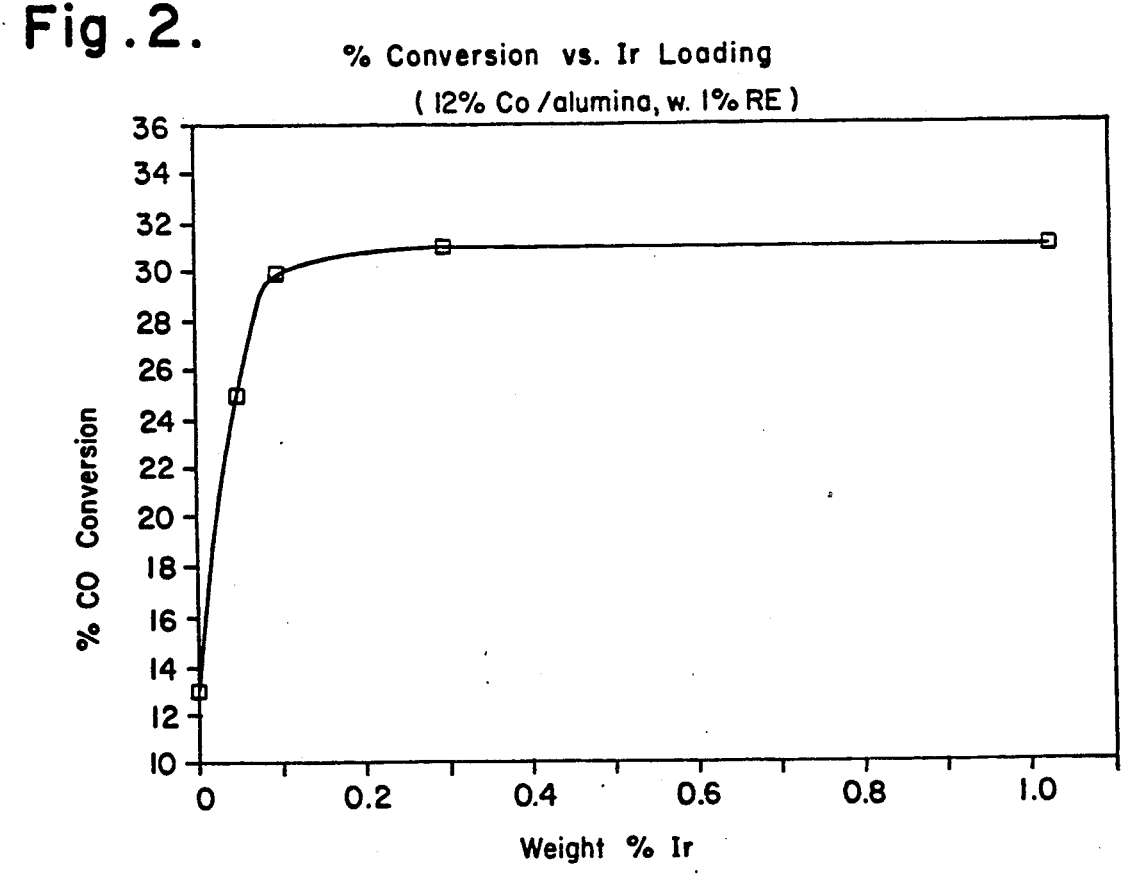
FIG. 2 is a graph showing carbon monoxide conversion versus iridium content for alumina supported catalysts containing cobalt plus iridium.
Figure 3:
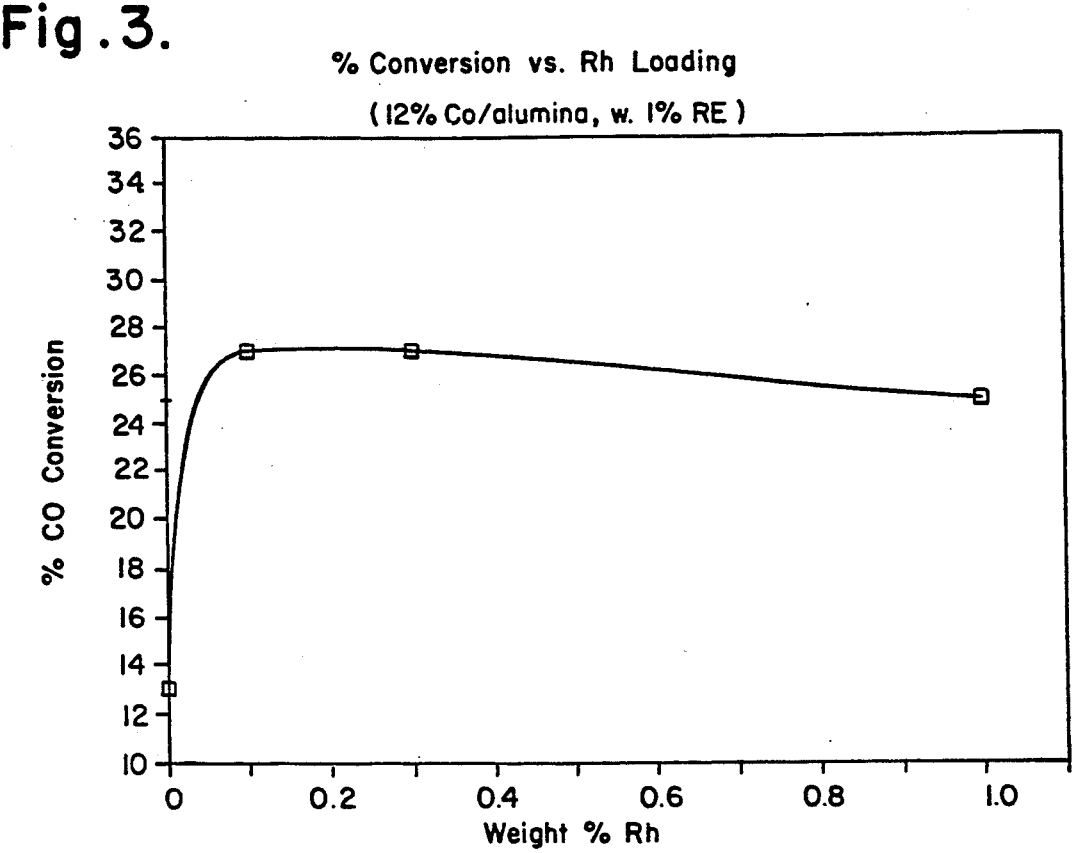
FIG. 3 is a graph showing carbon monoxide conversion versus rhodium content for alumina supported catalysts containing cobalt plus rhodium.

As can be seen in FIGS. 1, 2, and 3, the full effect of the second metal is achieved at a relatively low loading of that metal. For a catalyst containing 12 wt % Co, the maximum catalyst activity is observed at a second metal to Co weight ratio of about 0.01, where the second metal is Pt, Ir, or Rh. However, additional amounts of these second metals do not greatly affect the overall activity. Thus, a wide range of loadings of the second metal are possible without adversely affecting the large increase in catalytic activity achieved at low loadings of the second metal.

FIGS. 4, 5, and 6 show the improvement in catalytic activity of the Co catalyst upon addition of the second metal as the Co content is varied while keeping the weight ratio of second metal to cobalt equal to 0.0085.

The great improvement in carbon monoxide hydrogenation activity upon addition of small amounts of Pt, Ir, and Rh to supported cobalt catalysts appears to be unique for alumina supports. As can be seen by examining the data in Table VI, there is no improvement in activity upon addition of small, amounts of Pt, Ir, or Rh to cobalt supported on silica or titania. There is an, as yet undetermined, property of alumina which enables these second metals to greatly promote the dispersion of cobalt on this support. On silica and titania, absence of this property renders ineffective the ability of the second metal to disperse Co, resulting in no change in the catalytic activity. Other inorganic oxides possessing the same property as alumina would also be expected to exhibit enhanced activity upon addition of these second metals. Although we do not wish to be bound by the following explanation, it is possible that the reason alumina is so effective as a support for the catalysts of this invention is related to a complex relationship between the isoelectric point of the support and the charged species of the catalytic metals in solution at the pH of preparation.

Thus, Pt, Ir, and Rh may be added to Ru and Re, which have previously been found (see Kobylinski, U.S. Pat. No. 4,088,671 and Eri et al., U.S. Pat. No. 4,801,573) to greatly improve (by a factor of two or more) the activity of alumina-supported cobalt for hydrocarbon synthesis. This large increase in activity is not seen for other second metals, including other Group VIII transition metals, with the exception of Pd which exhibits loading sensitivity and is discussed in the following paragraph. The role of the second metal appears to be to help better disperse the cobalt. Attributes of the second metal which appear to be necessary to enhance the dispersion of cobalt are ease of reduction, ability to alloy with cobalt in the concentrations used, lack of a tendency to segregate to the cobalt surface, and possibly ability to interact with the alumina surface so as to provide an increase in nucleation sites for cobalt crystallite formation. It is possible that no single mechanism of promotion is operable for all the effective second metals.

Figure 7:
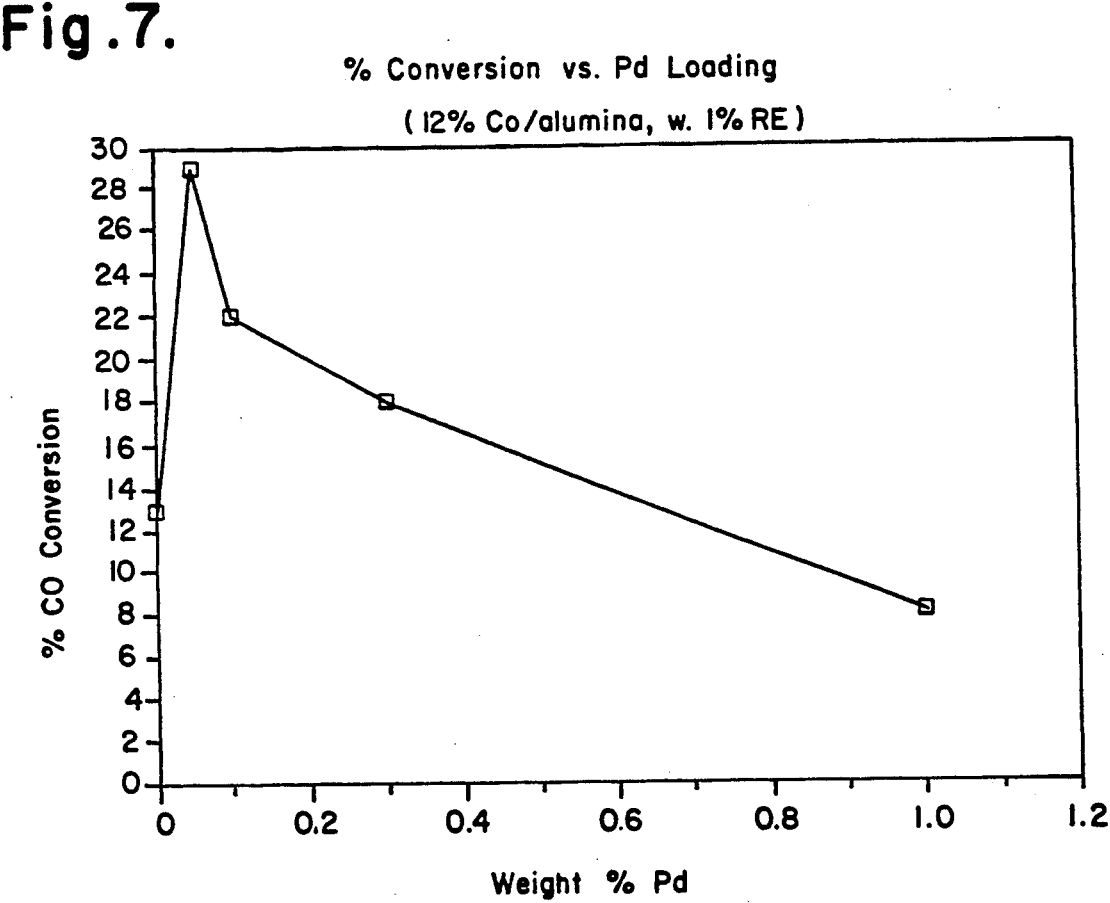
FIG. 7 is a graph showing carbon monoxide conversion versus palladium content for alumina supported catalysts containing cobalt plus palladium.

An attractive attribute of Pt, Ir, and Rh as additive metals for cobalt supported on alumina is that, while small amounts of these metals aid significantly in increasing tremendously the CO hydrogenation activity of the cobalt, larger amounts are not detrimental to this increased activity or the selectivity of the catalyst (see FIGS. 1-3). This behavior, herein defined as "loading-insensitivity", does not hold for all Group VIII metals or even all noble metals. For example, while the addition of limited amounts of Pd does increase the activity of the cobalt catalysts, the addition of larger quantities in the same range as that used for the catalysts with Pt, Ir, and Rh acts to reduce the CO hydrogenation activity to significantly less than that of cobalt on alumina catalysts containing no second metal additive (see FIG. 7).

Such a property as loading-insensitivity is an especially important characteristic for a minor (in terms of relative amount) component in a commercial catalyst. This permits the scale-up and manufacture of large quantities of a desired catalyst having reproducible, requisite characteristics. Commercial manufacture of catalysts containing components exhibiting sensitivity to loading can result in loss of activity or the desired selectivity as a result of uneven distribution of these components, even though the overall concentrations of these species is that found to be the ideal in laboratory trials.

What is claimed is:

1. A process for the production of hydrocarbons comprising the step of contacting a synthesis gas feed comprised of hydrogen and carbon monoxide with a catalyst consisting essentially of an amount of cobalt catalytically active in a Fischer-Tropsch synthesis, and at least one second metal selected from the group consisting of iridium, rhodium, and mixtures thereof composited on an alumina support, said second metal being present in relatively lesser amounts than the cobalt content of the catalyst, at a temperature, gas hourly space velocity and a pressure useful for promoting a Fischer-Tropsch Synthesis.

2. The process recited in claim 1 wherein said catalytically active amount of cobalt is up to about 60 wt. % of the catalyst.

3. A process for the production of hydrocarbons comprising the step of contacting a synthesis gas feed comprised of hydrogen and carbon monoxide with a catalyst consisting essentially of an amount of cobalt catalytically active in a Fischer-Tropsch synthesis, at least one second metal selected from the group consisting of iridium, rhodium, and mixtures thereof, and a promoter, wherein said promoter is an oxide of a metal selected from the group consisting of periodic groups IIIB, IVB, and VB, the lanthanides, the actinides, magnesium, and mixtures thereof, composited on an alumina support, said second metal being present in relatively lesser amounts than the cobalt content of the catalyst, said promoter ranging from about 0.1 to about 5 wt % of the catalyst, at a temperature, gas hourly space velocity and a pressure useful for promoting a Fischer-Tropsch Synthesis.

* * * * *

UNITED STATES PATENT AND TRADEMARK OFFICE
CERTIFICATE OF CORRECTION

PATENT NO. : 5,116,879
DATED : May 26, 1992
INVENTOR(S) : Sigrid Eri, James G. Goodwin, Jr., George Marcelin and Trygve Riis It is certified that error appears in the above-identified patent and that said Letters Patent is hereby corrected as shown below:

On the title page:
In References Cited, under Foreign Patent Documents, add --13-23742-Japanese--.

Col. 2, line 34, delete "entitles" and substitute therefore --entitled--.

Col. 12, line 18, delete "small," and substitute therefore --small--.

Signed and Sealed this

Second Day of November, 1993

Attest:

BRUCE LEHMAN

Attesting Officer     Commissioner of Patents and Trademarks